United States Patent [19]

Nagao et al.

[11] Patent Number: 4,676,905
[45] Date of Patent: Jun. 30, 1987

[54] FLUID SEPARATION METHOD AND APPARATUS

[75] Inventors: Shozo Nagao, Yasu; Naoyuki Mitani; Teruyuki Nakagawa, both of Otsu, all of Japan

[73] Assignee: Toray Industries, Inc., Tokyo, Japan

[21] Appl. No.: 750,508

[22] Filed: Dec. 14, 1976

[30] Foreign Application Priority Data

Dec. 15, 1975 [JP] Japan ................... 50-148440

[51] Int. Cl.$^4$ ............................................. B01D 13/00
[52] U.S. Cl. .................................. 210/646; 210/321.3; 210/416.1
[58] Field of Search ............... 210/22, 87, 321 B, 188, 210/195 R, 646, 929, 416.1; 137/99; 417/393, 395

[56] References Cited

U.S. PATENT DOCUMENTS

| 3,330,290 | 7/1967 | Porter | 137/99 |
| 4,008,003 | 2/1977 | Pinkerton | 137/99 X |
| 4,093,545 | 6/1978 | Cullis | 210/321 B X |
| 4,197,196 | 4/1980 | Pinkerton | 210/321.3 X |

OTHER PUBLICATIONS

McDonald, Jr., "An Automatic Peritoneal Dialysis Machine for Hospital or Home Peritoneal Dialysis: Preliminary Report", from vol. XV, Trans. Amer. Soc. Artif. Int. Organs, 1969, pp. 108-113.

Primary Examiner—Frank Spear
Attorney, Agent, or Firm—Austin R. Miller

[57] ABSTRACT

Fluid separation method and apparatus for simultaneously carrying out dialysis and ultrafiltration and exactly controlling the ultrafiltration rate is disclosed. The method and apparatus is concerned with a dialysis system comprising the combination of a fluid separating device; one or more units for dialysate each unit, each unit comprising a pair of dialysate chambers separated by at least one partition which is movable or transformable while keeping the over-all volume of a pair of dialysate chambers constant; a variable speed dialysate feed pump; a variable speed dialysate discharge pump; and other devices e.g. monitoring devices.

Fresh dialysate is fed from one of the dialysate chambers into the dialysate inlet of the fluid separating device; separation treatment is carried out through the semi-permeable membrane of the fluid separating device; waste dialysate is discharged from the dialysate outlet of the fluid separating device into the dialysate chamber and the over-all volume of this closed circuit is maintained constant. The controlled ultrafiltrate is exactly discharged from the closed circuit by an ultrafiltration pump; and a continuous operation is carried out in a plurality of units for exchanging dialysate alternately.

51 Claims, 11 Drawing Figures

FLUID SEPARATION METHOD AND APPARATUS

BACKGROUND OF THE INVENTION

This invention relates to the general field of separating fluids by means of their different permeation rates through a semi-permeable membrane. More specifically, the invention involves a new and improved, inexpensive, easily operable and compact separation apparatus of high dialysis efficiency for use in simultaneous dialysis and ultrafiltration by exactly controlling the amount of ultrafiltration rate.

Methods and apparatuses for fluid separation and concentration by the principle of dialysis and ultrafiltration through a semi-permeable membrane have been generally known. For example, these techniques have been heretofore used for separating or concentrating bacteria, protein, or colloidal substances in the manufacture of medicines or foods, and the hemodialysis procedure is a practical treatment in the medical field.

In many practical cases improvement of dialysis efficiency and exact control of a ultrafiltration rate are desired. Particularly, in the case of hemodialysis, when removing waste components and water from blood by dialysis and ultrafiltration, insufficient removal of waste components or inexact control of ultrafiltration rate may result in serious consequences to the patient. Excessive water removal may cause reduction of blood pressure or death from shock.

Although improvements in the efficiency of dialysis or exact control of the ultrafiltration rate are extremely important, conventional devices which have high dialysis efficiency are bound to have inaccurate ultrafiltration control. On the other hand, conventional devices with exact ultrafiltration control are found to have low dialysis efficiency.

The present invention and its advantages will be better understood in view of the present drawings wherein.

Figure 1:
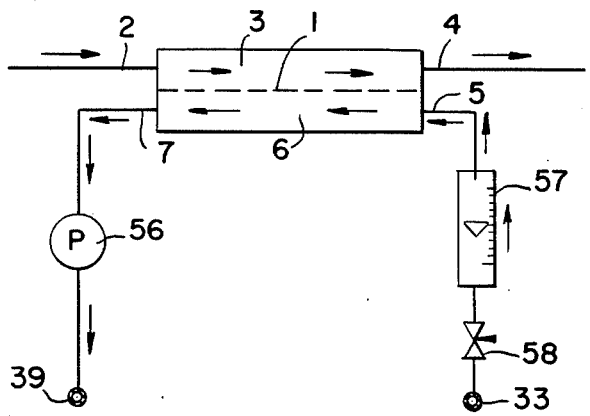
FIGS. 1, 2 and 3 are schematic illustrations of fluid separation apparatus of the prior art.

Referring to FIG. 1, according to the prior art the fluid to be treated is fed into the compartment 3 separated by a semi-permeable membrane 1 from a dialysate compartment 6 through an inlet 2, and is discharged through an outlet 4. On the other hand, fresh dialysate is fed into the dialysate compartment 6 from a fresh dialysate feed pipe 33 through a flow control valve 58, a flow meter 57, and then a dialysate inlet 5, and is discharged from dialysate compartments through a dialysate outlet 7 through a dialysate pump P and into a waste dialysate pipe 39.

In this operation, waste components are removed from a fluid having a high concentration of waste components to the dialysate having a low concentration of waste components through the membrane 1 in the fluid separating device 1, 3, 6. This phenomenon of dialysis is caused by the concentration difference of the waste components. The fluid separating device 1, 6 shown in FIG. 1 has a high dialysis efficiency because of the high concentration difference of waste components since fresh dialysate comes into interchange with already dialysed fluid through the membrane 1, since the respective fluids flow in a countercurrent manner.

On the other hand, the ultrafiltration rate has been sharply controlled by controlling the transmembrane pressure; the ultrafiltration rate is proportional to this pressure difference. However, in this way the ultrafiltration rate per unit transmembrane pressure varies every moment since colloidal materials in the fluid to be treated, such as proteins, lipids and blood cells in case of hemodialysis, deposit on the surfaces of the membrane thus interfering with accurate control of the ultrafiltration rate. Particularly, a device having high performance with a high flux membrane causes intolerably large variations of the ultrafiltration rate in spite of the small variations of the transmembrane pressure. Therefore, the conventional systems have these serious defects.

In order to overcome these defects, various methods and devices are known.

Typical patents relating to ultrafiltration control systems include Japanese Patent Laying-open Publications Numbers 48-76393 and 49-64291.

Figure 2:
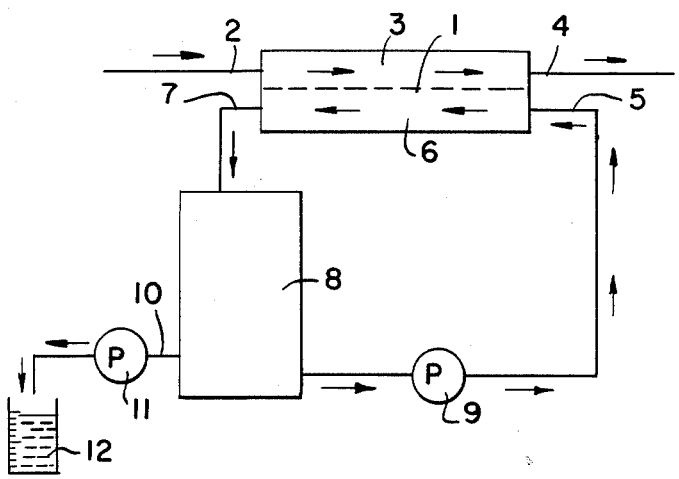

The principles of these methods are shown in FIG. 2. Referring to FIG. 2, the closed vessel 8 having a constant volume is connected into the dialysate fluid line, particularly to the dialysate inlet 5 and to the dialysate outlet 7 of the fluid separating device 1, 3, 6. Therefore, a closed circuit is formed.

Dialysis is carried out by circulating the dialysate fluid, using a dialysate circulating pump 9 in the closed circuit, and the ultrafiltrate is pumped out through a nozzle 10 of the closed vessel by an ultrafiltration pump 11. The removal rate of the ultrafiltrate is adjusted by measuring the fluid in the measuring cylinder 12.

In this method, the removal rate of the ulfiltrate is controlled more exactly than in the method as shown in FIG. 1, because the rate of ultrafiltration is independent of the trans-membrane pressure and can be determined exactly by means of the ultrafiltration pump and measuring cylinder.

However, in this method of FIG. 2, the dialysate fluid is recirculated and dialysate fluid of high waste concentration is mixed with the fresh dialysate fluid in the closed vessel 8. Therefore, the waste concentration of the dialysate in closed vessel 8 gradually increases during the dialysis procedure and the dialysis efficiency decreases with time due to the ever-decreasing concentration difference between the solutes in the fluids on either side of the semi-permeable membrane in the fluid separating device.

Figure 3:
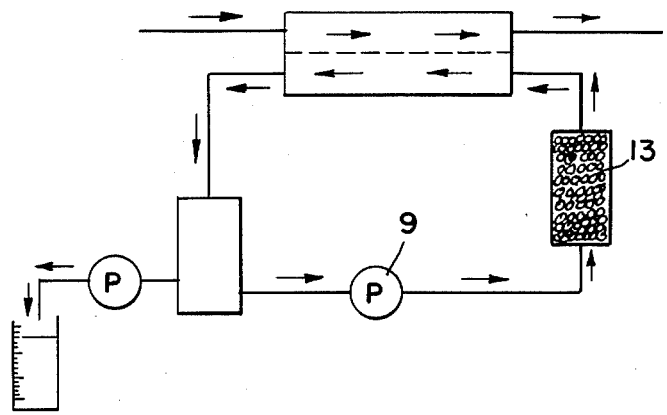

To prevent the increase of solute concentration of the dialysate in the vessel 8, the method shown in FIG. 3 has been proposed, in which method the solute is removed when the dialysate passes through an adsorption column 13 which is connected into the closed circuit. However, in this adsorption method the choice of an appropriate adsorbent is difficult.

In a hemodialysis apparatus, for example, no adequate proper adsorbent has yet been found for removing urea from the dialysate, which is transferred to the dialysate from the blood.

Generally, the adsorption method in the case of FIG. 3 has a lower dialysis efficiency than the single pass method shown in FIG. 1.

There is also a further defect in the methods shown in FIGS. 2 and 3 that scale from the solute in the dialysate attached itself to the walls of the whole apparatus as a scale because of the high solute concentration in the dialysate. This scale causes a volumetric rate change in the dialysate fluid flow and finally causes blockage in the dialysate fluid line.

To prevent this scale deposit, it is necessary to cleanse and sterilize the apparatus in the closed circuit dialysis. This increases costs of the dialysis.

We have now developed a fluid separation method and apparatus with exact controllability of the ultrafiltration rate, so as to overcome the said defects.

Our invention is concerned with a method of dialysis in which the ultrafiltration rate can be accurately controlled.

This invention is also concerned with a method in which the dialysis operation is performed with high efficiency, low cost and reduced difficulty. Our invention relates to a dialysis and ultrafiltration system which comprises a fluid separating device having a semi-permeable membrane and two or more dialysate chambers, each dialysate chamber being separated by means of a movable or displaceable partition.

One dialysate chamber is joined to a dialysate inlet of a fluid separating device and the other dialysate chamber is joined to a dialysate outlet of a fluid separating device. The fluid separating device and two or more dialysate chambers constitute a closed circuit. The method of our invention is featured by generating a circulation flow of the dialysate fluid in the closed circuit.

Our invention also comprises a fluid separating device which carries out dialysis and ultrafiltration simultaneously by contacting dialysate fluid with a fluid to be treated through a semi-permeable membrane, and two units, each of which includes two dialysate chambers separated by at least one movable or flexible partition. One of the two dialysate chambers of each unit is connected to the dialysate outlet of the fluid separating device and the other dialysate chamber is connected to the dialysate inlet of the fluid separating device.

Therefore these devices form two closed circuit lines as a whole. While a fluid separating process is carried out in one of the closed circuits so as to generate a flow, fresh dialysate is fed into the other unit with two dialysate chambers from the outside of the closed circuit, and waste dialysate is removed to the outside of the closed circuit.

The two closed circuit lines are switched to each other alternately.

Figure 4:
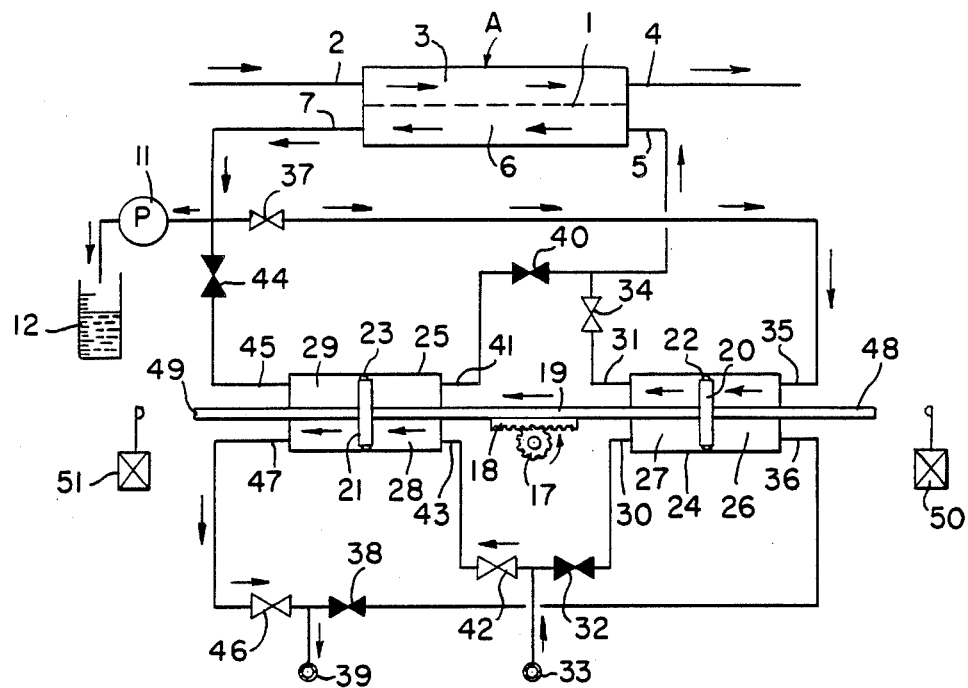
FIGS. 4, 5 and 6 are schematic illustrations of improved fluid separation apparatus of the present invention, each of which shows different operating stages of the apparatus.

FIG. 4 shows a fluid separating device A comprising a semi-permeable membrane 1, a compartment 3 for a fluid to be treated and a dialysate compartment 6. Through an inlet 2 passes the fluid to be treated. The fluid is fed into the compartment 3 which is isolated from the dialysate compartment 6 by means of the semi-permeable membrane 1. The fluid is dialyzed and ultrafiltered in compartment 3, and discharged through the outlet 4.

On the other hand, the dialysate fluid is fed and discharged as follows.

The rod 19 is movable in the longitudinal direction by means of the rack 18 and the pinion 17.

The pistons 20 and 21, which are fixed to the rod 19, have packings such as the O-rings 22, 23 respectively, and constitute isolating movable partitions which divide the unit 24, 25 into the pair of dialysate chambers 26, 27 and 28, 29, respectively.

The dialysate chamber 27 has an inlet 30 for dialysate which is connected with the feed pipe 33 for fresh dialysate through the valve 32. Also, the outlet 31 for fresh dialysate is connected with the dialysate inlet 5 of the fluid separating device A through a valve 34.

The dialysate chamber 26 has an inlet 35 for waste dialysate which is connected to the dialysate outlet 7 of the fluid separating device A through the valve 37. The outlet 36 for waste dialysate is connected to a return pipe 39 for waste dialysate through a valve 38.

Similarly, the dialysate chamber 28 has an outlet 41 for fresh dialysate which is connected to the dialysate inlet 5 of the fluid separating device A through the valve 40. The inlet 43 for fresh dialysate is connected to the fresh dialysate feed pipe 33 for fresh dialysate through a valve 42. The dialysate chamber 29 has an inlet 45 for waste dialysate connected with the dialysate outlet 7 of the fluid separating device A through the valve 44, and the outlet 47 for waste dialysate is connected through the valve 46 to the return pipe 39 for waste dialysate.

The limit switches 50 and 51 are located in a position to be operated by movement of the rods 48 and 49 which are fixed to the pistons 20 and 21 respectively.

By these limit switches, a unit 24 comprising a pair of dialysate chambers 26 and 27 is switched to the other unit 25 comprising a pair of the dialysate chambers 28 and 29.

FIG. 4 shows an example of a starting position in accordance with this invention.

Referring to FIG. 4, a closed dialysate circuit is formed comprising the dialysate chamber 27, the valve 34, the dialysate compartment 6 for dialysate of the fluid separating device A, the valve 37 and the dialysate chamber 26, when the valves 32, 38, 40, 44 are closed and the valves 34, 37, 42, 46 are open.

Now, concerning unit 24, the dialysate chamber 27 is filled with fresh dialysate and the dialysate chamber 26 is filled with waste dialysate.

When the pinion 17 is rotated by its motor (not shown in FIG. 4) in the direction of the arrow shown in FIG. 4, the volume of fresh dialysate chamber 27 decreases and the volume of waste dialysate chamber 26 increases, and the decreased volume and the increased volume are exactly equal when all the diameters of the rods 19, 48 and 49 are equal.

Therefore the fresh dialysate of the dialysate chamber 27 flows through the outlet 31, the valve 34 and the dialysate inlet 5 into the compartment 6 of the fluid separation device A. The fluid to be treated is dialyzed and ultrafiltered in the fluid separating device A and the waste dialysate flows into the dialysate chamber 26 through the dialysate outlet 7 of the fluid separating device A, the valve 37 and the inlet 35 for waste dialysate.

The waste dialysate in the dialysate chamber 26 does not mix with the fresh dialysate in the dialysate chamber 27, because the dialysate chamber 26 is isolated from the dialysate chamber 27 by means of the piston 20 and, a packing such as the O-ring 22.

On the other hand, concerning unit 25, when the piston 21 moves in the direction of the arrow shown in FIG. 4 by rotation of the pinion 17, fresh dialysate flows in the dialysate chamber 28 from the feed pipe 33 through the valve 42, the inlet 43 for fresh dialysate, and waste dialysate flows out of the dialysate chamber 29 into the return pipe 39 for waste dialysate through the outlet 47 and the valve 46.

As described above in detail, the unit 24 supplies the fluid separating device with fresh dialysate and, at the same time, the movement of piston 23 replaces waste dialysate in the unit 25 with fresh dialysate.

Figure 5:
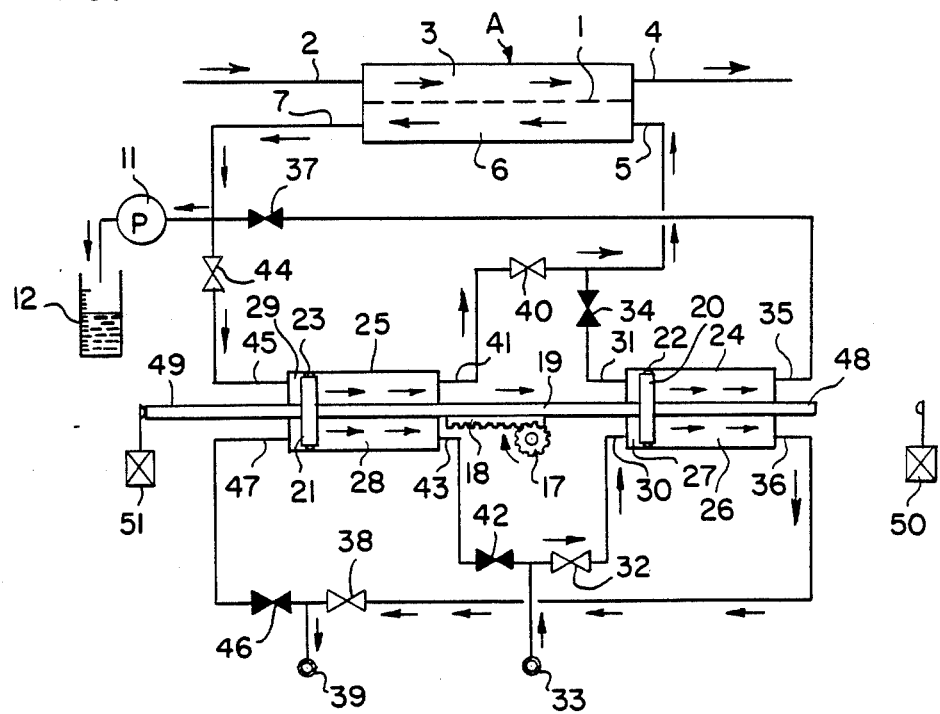

FIG. 5 shows the next operating stage of the system shown in FIG. 4.

When the rod 49 engages the limit switch 51 as shown in FIG. 5, the rotation of the pinion 17 is reversed and at the same time valves 32, 38, 40 and 44 are opened and valves 34, 37, 42 and 46 are closed.

Therefore, the functions of units 24 and 25 are exchanged with each other and unit 24 becomes charged with fresh dialysate and discharges the waste dialysate, and the unit 25 supplies the fluid chamber 6 with fresh dialysate and removes waste dialysate from chamber 6, so that dialysis and ultrafiltration are continued in the fluid separating device A.

Figure 6:
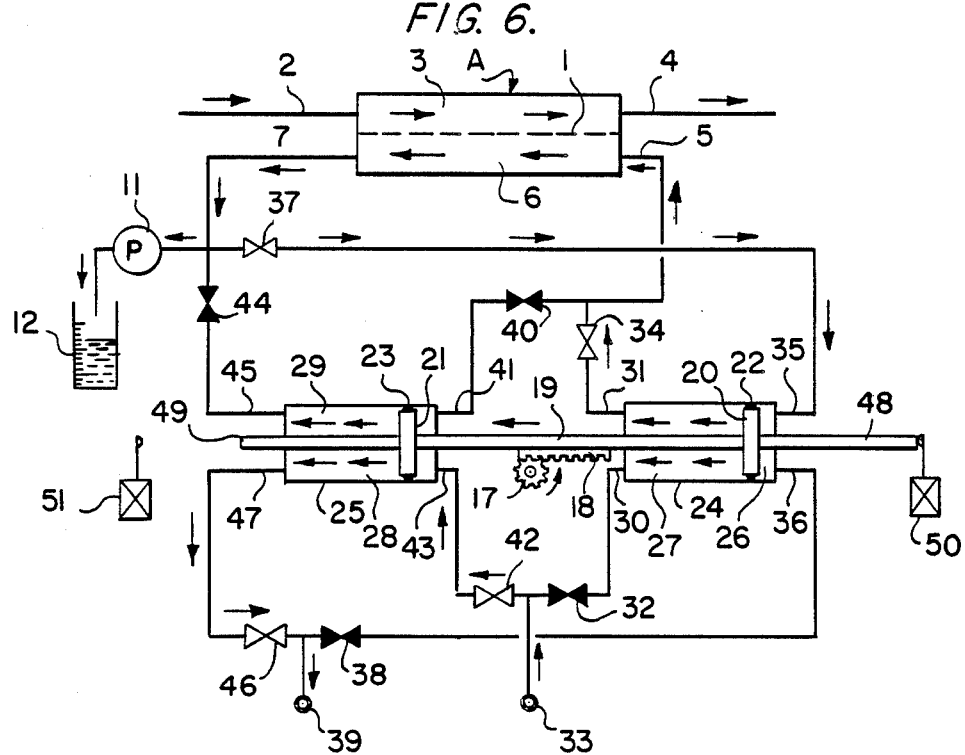

When the rod 48 engages the limit switch 50, as shown in FIG. 6, the rotation of the pinion 17 is again reversed and the valves 34, 37, 42 and 46 are opened, and the valves 32, 38, 40 and 44 are again closed at the same time. The functions of units 24 and 25 are again exchanged with each other. Therefore, dialysis and ultrafiltration are continued in the fluid separating device A.

As described above in detail, by exchanging the functions of units 24 and 25, the fluid separating device A is continued to be supplied with fresh dialysate. This dialysate line is substantially closed and ultrafiltration is carried out very precisely, with the ultrafiltration pump 11 measuring the amount of ultrafiltration by utilizing the measuring vessel 12 as shown in FIG. 4.

This invention enables the operator to maintain a high efficiency of dialysis, as described above, because fresh dialysate always flows into the fluid separating device and the operator can carry on very precise ultrafiltration because the dialysate circuit is substantially closed.

Furthermore, the present invention is not limited to the one embodiment as shown in FIGS. 4–6.

For example, the driving mechanisms of the rod 19 need not only be the pinion 17 and the rack 18 of FIG. 4, but may be other well known means such as a screw mechanism or a driving mechanism.

Figure 7:
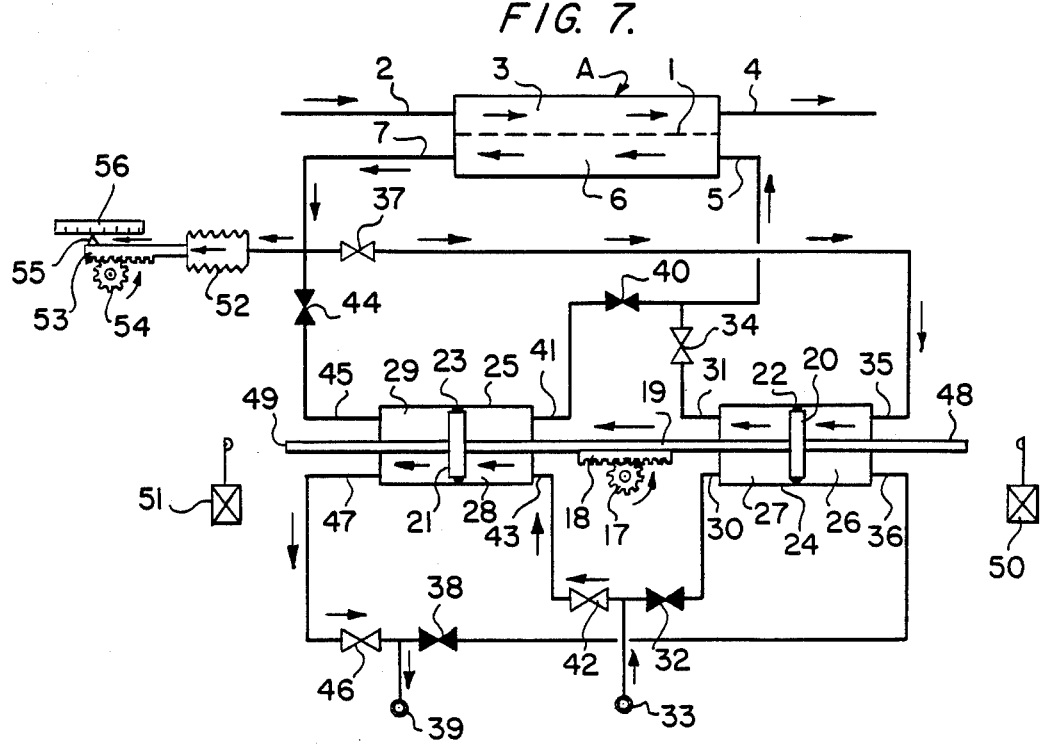
FIGS. 7, 8, 9, 10 and 11 each represents a schematic illustration of a different embodiment of the present invention.

FIG. 7 shows another embodiment of the present invention comprising a bellows 52, a rack 53 and a pinion 54 instead of the ultrafiltration pump 11 shown in FIG. 4.

By expanding the bellows by means of the rack 53 and the pinion 54, the ultrafiltered fluid is stored in the bellows, and its amount is measured by means of a scale 56 and an indicator 55. It is an advantage of this embodiment of the present invention shown in FIG. 7, that makes it a safe, steady, inexpensive and leakless apparatus because it does not pump out the ultrafiltered fluid from a closed circuit.

Figure 8:
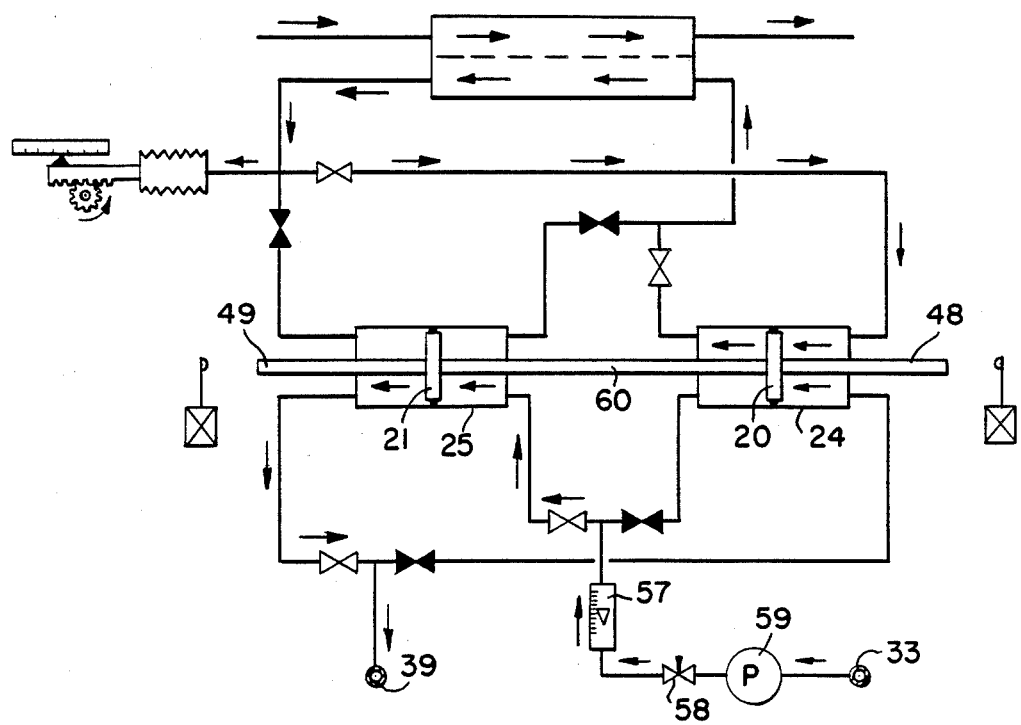

FIG. 8 shows another embodiment of the present invention. In the method of FIG. 7, a rack and a pinion move the pistons 20, 21, but in the method of FIG. 8, delivery pressure by the pump 59 moves pistons 20, 21 and an amount of pressure depending on the capacity of the pump 59 is supplied into the fluid separating device A.

The present invention is compatible with the well-known method of FIG. 1 since both can share the pump 59, the rotameter 57 and other parts.

The advantage of this embodiment is that it can be easily substituted for the conventional method in FIG. 1.

It is difficult to change valves and to reverse the rack and the pinion at the same time because it takes some time to reverse the rack and the pinion which are the driving force of the dialysate. Therefore, the method shown in FIG. 7 has the problem that large shocks are experienced in the dialysate flow. However, the embodiment shown in FIG. 8 has the advantage that the dialysate flow is less disturbed when switching valves since the flow direction of pump discharge is changed only by the valves.

Figure 9:
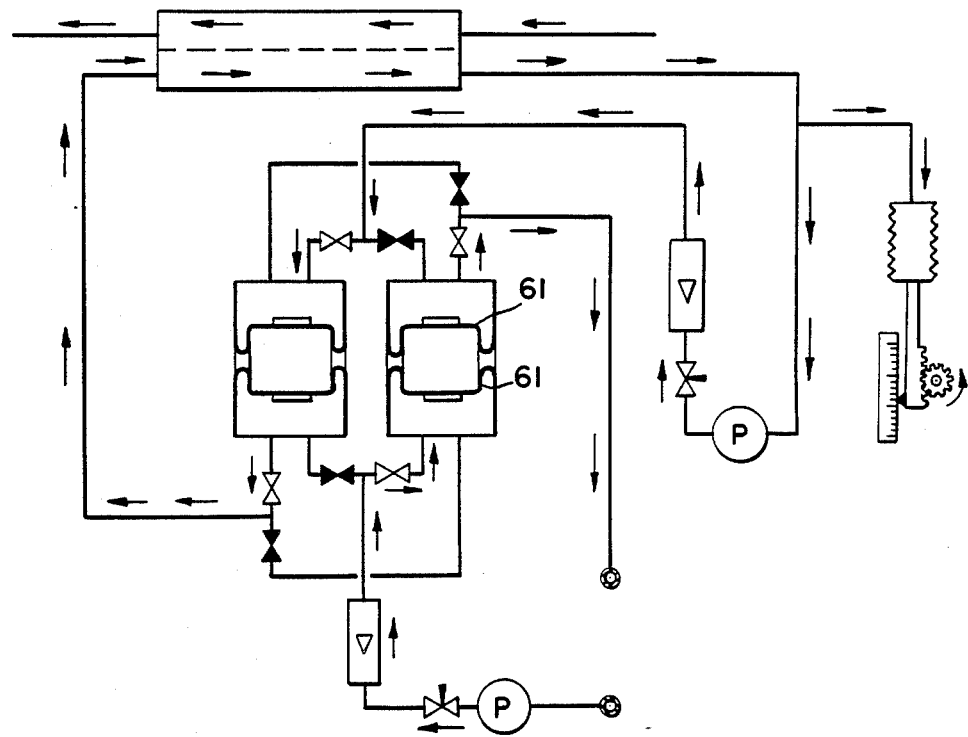

FIG. 9 shows another embodiment of this invention. This embodiment uses the diaphragm packing 61 instead of the rod 48, 49 and the connecting rods 60 of the unit 24, 25 as shown in FIG. 8. Compared with the system shown in FIG. 8, there is less trouble from leaking from the packings since fresh dialysate and waste dialysate are separated completely by the diaphragms, and waste dialysate is prevented from contaminating the fresh dialysate due to leakage of dialysate waste deposited on the wall of the unit 24, 25 and later removed by the O-rings 22, 23.

Figure 10:
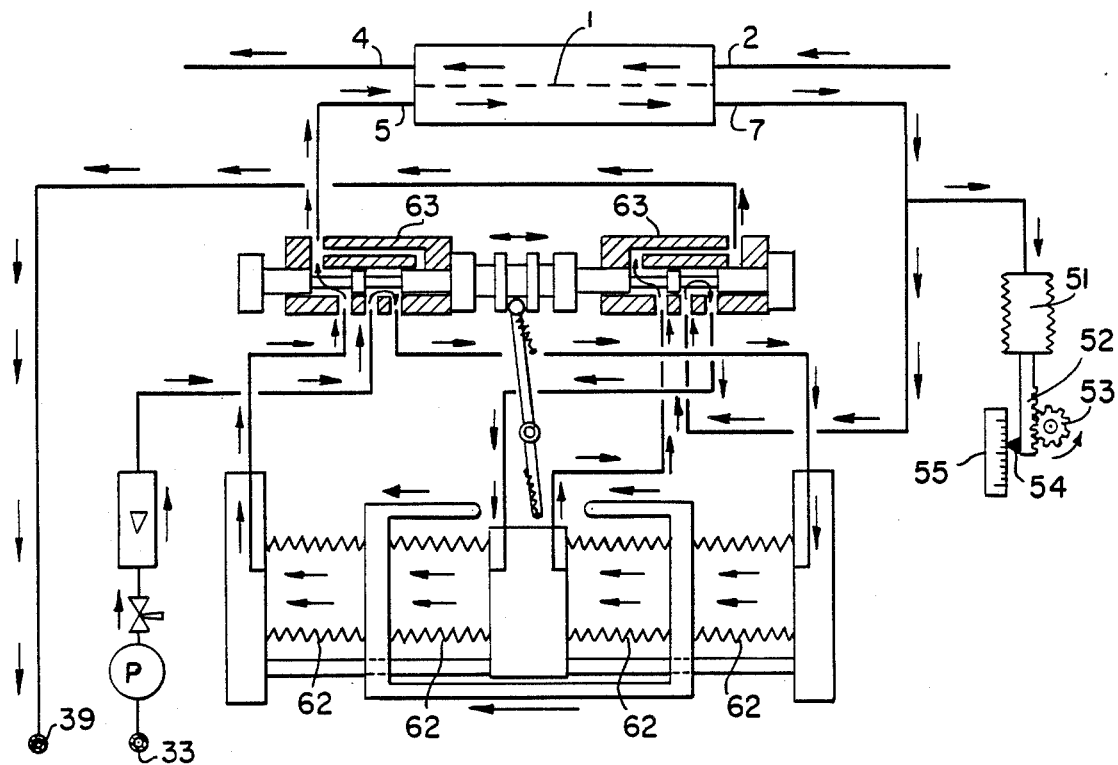

FIG. 10 shows another embodiment of the invention. The difference from the system shown in FIG. 9 is in the use of flexible bellows 62 in place of the cylinder, and a four way valve 63 as the switching valve operated by displacement of the bellows 62.

The bellows can be disposed of when it is contaminated by dialysate waste so as to avoid laborious cleaning work. the disposable bellows has great advantages since it is unnecessary to clean and sterilize with every dialysis operation utilizing an artificial kidney.

In FIG. 10 a flexible rubber balloon is shown instead of the bellows since it has the same advantage as the bellows.

Figure 11:
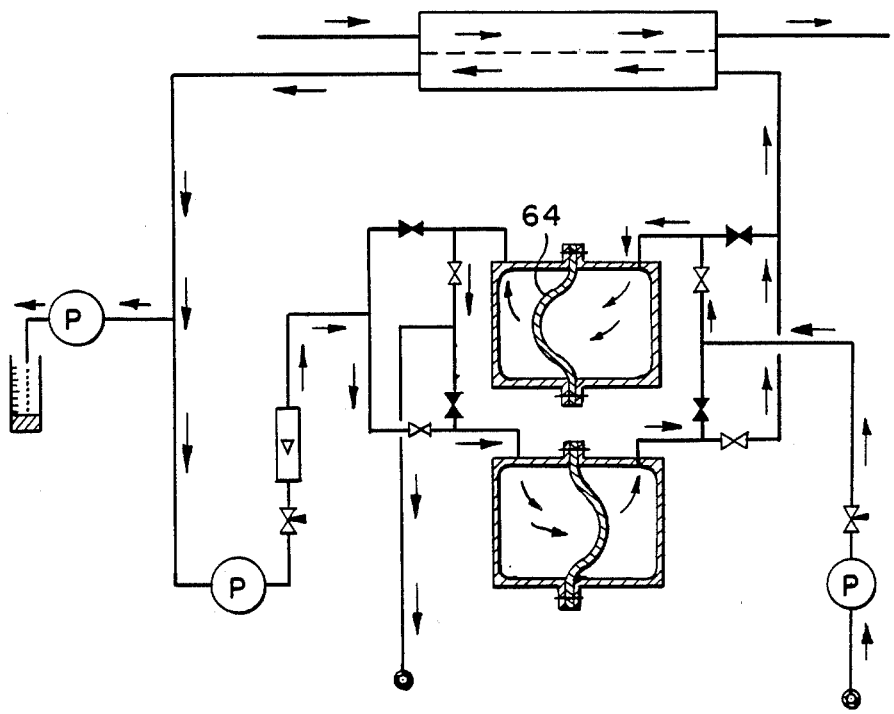

The embodiment shown in FIG. 11 has almost the same structure and advantages as the embodiment of FIG. 9. However, an elastic or flexible diaphragm 64 is used instead of the displacing partition.

The dialysate flow can be generated either by displacement of a diaphragm or by pumps inserted in the closed circuit lines. This invention is not limited to embodiments shown in FIGS. 5–11 as already explained in detail, but it can be conducted with the combination of each of the elements in these examples and of conventional methods which have similar functions.

This invention is not limited to the flat membrane type of the fluid separating device but can also be applied to the hollow fiber type, to the coil type and to any type of fluid separating device.

Excess trans-membrane pressure will occur occasionally but ultrafiltration is carried out regardless of trans-membrane pressure in this invention. The safety equivalent to the conventional method can be secured by providing a trans-membrane pressure gage to monitor the pressure relating to the breakage pressure of the membrane.

By applying this invention, it has been proven that the ultrafiltration rate can be accurately controlled and high dialysis efficiency can be obtained for a fluid separating device of high ultrafiltration rate, e.g. 3.5 ml/Hr. mmHg and over, which is not practical by the conventional method. Therefore, combining the method of this invention with a fluid separating device which has a high ultrafiltration rate per unit trans-membrane pressure, we can achieve ultrafiltration and dialysis in a very short time, which is impossible by any conventional method.

It is necessary to use a high efficiency fluid separating device with a high ultrafiltration rate per unit transmembrane pressure and a high dialysis efficiency to perform ultrafiltration and dialysis rapidly.

The combination of the high efficiency fluid separating device and the conventional system shown in FIG. 1 is impractical because it cannot accurately control the ultrafiltration rate.

In the case of the system shown in FIG. 2, there can be an accurate control of the ultrafiltration rate but the dialysis efficiency will decrease in time and a long dialysis time will be required. On the contrary, the combination of this invention and a high efficiency fluid separating device can complete the necessary ultrafiltration and dialysis procedure in a short time because it can control the ultrafiltration rate accurately and because the dialysis efficiency does not decrease in time as described hereinbefore.

As hereinbefore described, this invention in combination with a high efficiency fluid separating device can provide an excellent, inexpensive and trouble-free fluid separating method which can complete ultrafiltration and dialysis in a short time and also which can accurately control the ultrafiltration rate without a decrease in dialysis efficiency.

We claim:

1. In a method for separating components of fluid through a fluid separating device having a fresh dialysate inlet and a waste dialysate outlet and having a semi-permeable membrane effective to perform simultaneous dialysis and ultrafiltration, in an apparatus in which said fluid separating device is connected to at least two dialysate chambers each having at least one movable partition arranged to form separate dialysate units, said dialysate units having essentially equal volume, the improvement which comprises conducting an accurately measured quantity of fresh dialysate fluid from one dialysate unit of a first dialysate chamber to said dialysate inlet of the fluid separating device and concurrently withdrawing waste dialysate fluid from said dialysate outlet of the fluid separating device and returning it to another dialysate unit of said first dialysate chamber, all in a closed circuit, then establishing a separate closed circuit and conducting the same accurately measured quantity of fresh dialysate fluid from one dialysate unit of a second dialysate chamber to said dialysate inlet of said fluid separating device and concurrently withdrawing waste dialysate fluid from said dialysate outlet of said fluid separating device and returning it to another dialysate unit of said second dialysate chamber, all in said separate closed circuit, and continuously alternating operation of said two closed circuits while feeding equal fluid quantities to said units in each cycle, and measuring the amount of ultrafiltration by measuring the excess of dialysate fluid being withdrawn from a closed circuit, said excess being defined by the amount of waste dialysate fluid withdrawn from said fluid separating device which is greater than said quantity of fresh dialysate fluid admitted to said fluid separating device during each said cycle.

2. The method in claim 1, wherein the ultrafiltration co-efficient of said fluid separating device is at least 3.5 ml/Hr.mmHg.

3. The method in claim 1, including displacing said partition so that the dialysate flow in said closed circuit is generated.

4. The method of claim 1, including generating the dialysate flow in said closed circuit by a pump inserted in said closed circuit.

5. The method in claim 1, wherein said fluid to be dialyzed and ultrafiltrated is blood.

6. Method as defined in claim 1 wherein said measuring comprises removing said excess fluid from said closed circuit by means of a pump which is connected to a measuring vessel.

7. Method as defined in claim 1 wherein said measuring comprises expanding said closed circuit and storing said excess in the expanded portion of said closed circuit, and providing a measuring device in operative association with said expanded portion for measuring the amount of ultrafiltration.

8. In an apparatus for separating components of fluid, the combination which comprises a fluid separating device having a fresh dialysate inlet and a waste dialysate outlet and having a semi-permeable membrane effective to perform simultaneous dialysis and ultrafiltration, said apparatus comprising at least two dialysate chambers connected to said fluid separating device, each said dialysate chamber having at least one movable partition arranged to form separate dialysate units, said dialysate units having essentially equal volumes, a separate isolated circuit connected to conduct fresh dialysate fluid from one dialysate unit of a first dialysate chamber to said dialysate inlet of said fluid separating device and to conduct waste dialysis fluid from said dialysate outlet of said fluid separating device to another dialysate unit of said first dialysate chamber, another separate isolated circuit connected to conduct fresh dialysate fluid from one dialysate unit of a second dialysate chamber to said dialysate inlet of said fluid separating device and to conduct waste dialysate fluid from said dialysate outlet of said fluid separating device to another dialysate unit of said second dialysate chamber, means for continuously and automatically switching the operation of one of said circuits to the operation of the other circuit, each exclusively of the other, and for providing feeds of essentially equal quantities of fresh dialysate fluids to said separating device, with each cycle, and measuring means for measuring the amount of ultrafiltration by means of the excess of dialysate fluid being withdrawn from an isolated circuit, said excess being defined by the amount of waste dialysate fluid withdrawn from said separating device which is greater than said quantity of fresh dialysate fluid admitted to said separating device during each said cycle.

9. The apparatus in claim 8, wherein the ultrafiltration co-efficient of said fluid separating device is at least 3.5 ml/Hr.mmHg.

10. The apparatus in claim 8, wherein said partition of said dialysate chamber is a diaphragm.

11. The apparatus in claim 10, wherein said diaphragm is an elastic membrane.

12. The apparatus in claim 8, wherein said partition of said dialysate chamber is a bellows.

13. The apparatus in claim 8, wherein said partition of said dialysate chamber is a sliding rigid wall.

14. The apparatus in claim 8, wherein said partition of said dialysate chamber is the combination of a sliding rigid wall and a diaphragm.

15. The apparatus of claim 8, wherein said dialysate flow is generated by means of displacing said partitions of said dialysate chambers.

16. The apparatus of claim 8, including a pump inserted in said closed circuit for generating dialysate flow.

17. The apparatus of claim 8, including means for detecting the pressure of said dialysate fluid or the fluid to be dialyzed and ultrafiltered.

18. The apparatus fo claim 8, wherein the fluid to be dialyzed and ultrafiltered is blood.

19. The apparatus of claim 8, wherein said partition of said dialysate chamber is the combination of a sliding rigid wall and a bellows.

20. Apparatus as defined in claim 8 wherein said measuring means comprise a pump and a measuring vessel connected to said pump, said pump being connected to said closed circuit for pumping said excess fluid into said measuring vessel.

21. Apparatus as defined in claim 8 wherein said measuring means comprise expansion means connected to said closed circuit, and a measuring device associated with said expansion means, said expansion means being adapted to receive said excess fluid, and whereby the amount of said excess fluid is measured by said measuring device.

22. In a fluid system comprising a filled hydraulic circuit for conducting a first fluid through a fluid processing container for admixture with a second fluid, thereby producing a mixture fluid from said first and second fluids, the combination which comprises:

(a) a pair of receptacles spaced apart from said container, each said receptacle having movable partition means dividing each of said receptacles into a pair of separate chambers, thereby providing a total of four separate chambers, two of said chambers being connected to supply said first fluid to said fluid processing container and two of said chambers being connected to receive mixture fluid therefrom, (b) rigid connecting means extending between the respective partition means for moving said partition means through equal increments for producing the same extent of reciprocating movement of both of said partition means in both of said receptacles, (c) fluid inlet means for said first fluid connected to said circuit for delivering said first fluid to either of the first chambers, (d) outlet means connected for removal of fluid mixture for discharge from the system, (e) mixture connections extending from both said mixture fluid chambers for delivering said mixture fluid from either of said mixture fluid chambers to said outlet means, (f) a pair of circulatory fluid circuits for said first fluid, each said circuit extending from a first fluid chamber to a mixture fluid chamber, each of said circulatory fluid circuits including (g) a common section which is common to each of said circulatory fluid circuits, and each said circulatory fluid circuit including inlet and outlet connections extending into and from said fluid processing container, said fluid processing container including (h) a second fluid inlet communicating with said common section and through which said second fluid is admitted to that common section to move in admixture with the first fluid from said processing container to either of said mixture fluid chambers, (i) first fluid valve means and mixture fluid valve means respectively associated with said fluid inlet means and said mixture fluid connections and effective to permit controlled movement of the partition means, and (j) a fluid removal conduit connected to said common section and constituting means for removing fluid from the circuit in quantities equal to the quantities of the second fluid admitted to the common section, whereby both said circulatory fluid circuits and said fluid removal conduit are constituted as a filled, sealed and enclosed constant volume hydraulic system.

23. A fluid handling system as claimed in claim 22, wherein said second fluid inlet is constituted by a membrane of a dialysis cell, said first fluid comprising a fresh dialysate solution and said second fluid comprising blood wastes, said cell being disposed in said common section, and wherein a mixture of blood wastes and dialysate is discharged from either of said mixture fluid chambers.

24. The fluid system defined in claim 22, further characterized by the fact that each of said receptacles is divided into a first fluid chamber and a mixture fluid chamber, and by the further fact that each of said circulatory fluid circuits (f) is confined to a single receptacle.

25. A fluid handling system comprising a filled hydraulic circuit including a pair of receptacles each having movable partition means dividing said receptacles into first and second chambers, means for producing reciprocation of said partition means, a first fluid inlet to said circuit for delivering first fluid to each of said first chambers, a connection from said first chamber of said one receptacle to said second chamber of said one receptacle, a connection between said first chamber of said other receptacle and said second chamber of said other receptacle, said connections including a common section, a second fluid inlet into said common section through which second fluid is admitted to that section to move with the first fluid to said second chambers, valve means operatively associated with said first inlet and said connections and effective to permit controlled movement of the partition means and fluid removal means connected to said common section and constituting means for removing fluid from the circuit in quantities equal to the quantities of the second fluid admitted to the circuit, whereby said circuit is constituted as a filled, constant volume hydraulic system.

26. A fluid handling system as claimed in claim 25, wherein said second fluid inlet is constituted by a membrane of a dialysis cell, said first fluid comprising a fresh dialysate solution and said second fluid comprising blood wastes, said cell being disposed in said common section and wherein a mixture of blood wastes and dialysate is discharged from said second chamber.

27. A fluid handling system as claimed in claim 26 wherein ultrafiltration co-efficient of said dialysis cell is at least 3.5 ml/Hr mmHg.

28. A fluid handling system as claimed in claim 25 wherein said fluid removal means are connected to deliver said removed fluid quantities to measuring means.

29. A fluid handling system as claimed in claim 25 wherein said partition means is a piston slidable in said receptacle.

30. A fluid handling system as claimed in claim 29 wherein said piston is freely supported in said receptacle and wherein said means producing reciprocation thereof comprises hydraulic means.

31. A fluid handling system as claimed in claim 29 wherein piston rod elements are projected from opposite ends of said piston and to the exterior of said chambers.

32. A fluid handling system as claimed in claim 31 wherein mechanical drive means is secured to said piston elements.

33. A fluid handling system as claimed in claim 25 wherein said receptacle comprises a housing and said partition comprises a flexible diaphragm member.

34. A fluid handling system as claimed in claim 25 wherein said dialysis membrane means constitutes said second fluid inlet, and said fluid removal means comprises an outlet opening from said common section.

35. A fluid handling system as claimed in claim 25 wherein said fluid removal means comprises metering pump means the inlet of which is connected to said common section.

36. A fluid handling system as claimed in claim 25 wherein said fluid removal means comprises expansion means.

37. A fluid handling system as claimed in claim 25 wherein a pump is provided in said common section.

38. A fluid handling system as claimed in claim 25 wherein each of said receptacles comprises a bellows.

39. A fluid handling system as claimed in claim 25, including means for detecting the pressure of said dialysate fluid or the fluid to be dialyzed and ultrafiltrated.

40. An apparatus for hemodialyzing which comprises
(1) a separate device having
  (1-1) a dialysate fluid pass having
    (1-1-1) a first inlet for fresh dialysate fluid and
    (1-1-2) a first outlet for spent dialysate fluid,
  (1-2) a blood pass having
    (1-2-1) a second inlet for blood to be dialyzed and
    (1-2-2) a second outlet for blood dialyzed, and
  (1-3) a semi-permeable membrane separating the dialysate fluid pass and the blood pass,
(2) a first dialysate fluid chamber having
  (2-1) a movable partition arranged to divide said chamber into at least two chamber portions to form
    (2-1-1) a first chamber portion having
      (2-1-1-1) a third inlet for fresh dialysate fluid and
      (2-1-1-2) a third outlet for fresh dialysate fluid and
    (2-1-2) a second chamber portion having
      (2-1-2-1) a fourth inlet for spent dialysate fluid and
      (2-1-2-2) a fourth outlet for spent dialysate fluid,
(b 3) a second dialysate fluid chamber having
  (3-1) a movable partition arranged to divided said chamber into at least two chamber portions to form
    (3-1-1) a third chamber portion having
      (3-1-1-1) a fifth inlet for fresh dialysate fluid and
      (3-1-1-2) a fifth outlet for fresh dialysate fluid and
    (3-1-2) a fourth chamber portion having
      (3-1-2-1) a sixth inlet for spent dialysate fluid and
      (3-1-2-2) a sixth outlet for spent dialysate fluid,
(4) the first dialysate fluid chamber portions having essentially equal volumes, and said second dialysate fluid chamber portions having essentially equal volumes,
(5) a first main feed line for fresh dialysate fluid one end of which is connected to an inlet of fresh dialysate fluid and the other end of which is connected to
  (5-1) a first branch feed line connected to the third inlet and
  (5-2) a second branch feed line connected to the fifth inlet,
(6) one part of main delivery line for fresh dialysate fluid one end of which is connected to the first inlet and the other end of which is connected to
  (6-1) a first branch delivery line connected to the third outlet and
  (6-2) a second branch delivery line connected to the fifth outlet,
(7) another part of the main delivery line for spent dialysate fluid one end of which is connected to the first outlet and the other end of which is connected to
  (7-1) a third branch delivery line connected to the fourth inlet and
  (7-2) a fourth branch delivery line connected to the six inlet,
(8) a second main feed line for spent dialysate fluid one end of which is connected to an outlet of spent dialysate fluid and the other end of which is connected to
  (8-1) a third branch feed line connected to the fourth outlet and
  (8-2) a fourth branch feed line connected to the sixth outlet,
(9) means for continuously and automatically switching from the operation of one group of lines comprising the first branch delivery line, the third branch delivery line, the second branch feed line and the fourth branch feed line to the operation of the other group of lines comprising the second branch delivery line, the fourth branch delivery line, the first branch feed line and the third branch feed line, each exclusively of the other, and for providing feeds and withdrawals of essentially equal quantities of fresh dialysate fluid and spent dialysate fluid to and from the separating device, with each cycle, and
(10) measuring means for measuring the amount of ultrafiltration by measuring the excess of dialysate fluid being withdrawan from the main delivery line, excess being defined by the amount of spent dialysate fluid withdrawn from the separating device which is greater than the quantity of fresh dialysate fluid admitted to the separating device during each cycle.

41. An apparatus for hemodialyzing as claimed in claim 40 wherein the movable partition comprises a piston slidable in the dialysate fluid chamber.

42. An apparatus for hemodialyzing which comprises
(1) a separating device having
  (1-1) a dialysate fluid pass having
    (1-1-1) a first inlet for fresh dialysate fluid and
    (1-1-2) a first outlet for spent dialysate fluid,
  (1-2) a blood pass having
    (1-2-1) a second inlet for blood to be dialyzed and
    (1-2-2) a second outlet for blood dialyzed,
  (1-3) a semi-permeable membrane separating the dialysate fluid pass and the blood pass,
(2) a first dialysate fluid chamber having
  (2-1) a movable partition arranged to form
    (2-1-1) a first chamber portion having
      (2-1-1-1) a first inlet-outlet for fresh dialysate fluid and
    (2-1-2) a second chamber portion having (2-1-2-1) a second inlet-outlet for spent dialysate fluid,
(3) a second dialyste fluid chamber having
  (3-1) a movable partition arranged to form
    (3-1-1) a third chamber portion having
      (3-1-1-1) a third inlet-outlet for fresh dialysate fluid and
    (3-1-2) a fourth chamber portion having
      (3-1-2-1) a fourth inlet-outlet for spent dialysate fluid,
(4) the first and second dialysate fluid chambers having essentially equal volumes,
(5) a first main feed line for fresh dialysate fluid one end of which is connected to an inlet of fresh dialysate fluid and the other end of which is connected to
  (5-1) a first branch feed line connected to a first inlet-outlet line which is connected to the first inlet-outlet and
  (5-2) a second branch feed line connected to a second inlet-outlet line which is connected to the third inlet-outlet,
(6) one part of a main delivery line for dialysate fluid one end of which is connected to the first inlet and the other end of which is connected to
  (6-1) a first branch delivery line connected to the first inlet-out line and
  (6-2) a second branch delivery line connected to the second inlet-outlet line,
(7) another part of the main delivery line for dialysate fluid one end of which is connected to the first outlet and the other end of which is connected to
  (7-1) a third branch delivery line connected to a third inlet-outlet line which is connected to the second inlet-outlet and
  (7-2) a fourth branch delivery line connected to a fourth inlet-outlet line which is connected to the fourth inlet-outlet,
(8) a second main feed line for spent dialysate fluid one end of which is connected to an outlet for spent dialysate fluid and the other end of which is connected to
  (8-1) a third branch feed line connected to the third inlet-outlet line and
  (8-2) a fourth branch feed line connected to the fourth inlet-outlet line,
(9) means for continuously and automatically switching from the operation of one group of lines comprising the first branch delivery line, the third branch delivery line, the second branch feed line and the fourth branch feed line to the operation of the other group of lines comprising the first branch feed line, the third branch feed line, the second branch delivery line and the fourth branch delivery line, each exclusively of the other, and for providing feeds and withdrawals of essentially equal quantities of fresh dialysate fluid and spent dialysate fluid to the separating device, with each cycle, and
(10) measuring means for measuring the amount of ultrafiltration by measuring the excess of dialysate fluid being withdrawn from the main delivery line, the excess being defined by the amount of spent dialysate fluid withdrawn from the separating device which is greater than the quantity of fresh dialysate fluid admitted to the separating device during each cycle.

43. An apparatus for hemodialyzing as claimed in claim 42 wherein the movable partition comprises a flexible diaphragm member.

44. In combination with a dialysis apparatus having an inlet for fresh dialysate fluid and an outlet for waste dialysate fluid, fluid handling apparatus which comprises:
  (a) means forming a first filled hydraulic circuit for causing fresh dialysate to flow through said inlet and for causing waste dialysate to flow from said outlet, said circuit including a chamber for delivering a predetermined volume of fresh dialysate to said inlet and a chamber of dialysate to said inlet and a chamber of equal volume for receiving an equal volume of waste dialysate from said outlet,
  (b) means forming a second filled hydraulic circuit operative in alternating sequence with said first circuit for causing fresh dialysate to flow through said inlet and for causing waste dialysate to flow through from said outlet, said second circuit including a chamber for delivering a predetermined volume of fresh dialysate to said inlet and a chamber of equal volume for receiving an equal volume of waste dialysate from said outlet, and
  sequencing means for operating said first and second circuits in alternating sequence.

45. The combination defined in claim 44, wherein means are provided for taking off waste dialysate fluid in an amount essentially equal to the amount dialysed.

46. The combination defined in claim 45, wherein means are provided for measuring the amount of waste dialysate fluid taken off.

47. The combination defined in claim 45, wherein said sequencing means is operative and effective to connect and disconnect said first and second circuits to and from said dialysate inlet.

48. The combination defined in claim 47, further comprising (a) first circuit supply means connected for supplying fresh dialysate solution to a chamber of said first filled hydraulic circuit and for simultaneously discharging the other chamber of said first circuit to waste, when said first circuit is disconnected from said dialysate inlet and outlet, (b) second circuit supply means connected for supplying fresh dialysate solution to a chamber of said second filled hydraulic circuit and for simultaneously discharging the other chamber of said second circuit to waste when said second circuit is disconnected from said dialysate inlet and outlet, and (c) sequencing means for alternately operating said first and second circuit supply means in timed relation to each other.

49. In a method of performing dialysis by causing fluid flow through a semi-permeable membrane for removal of waste components from a fluid to be treated, wherein fresh dialysate fluid is introduced into contact with said membrane and waste dialysate fluid is removed from contact with said membrane, the steps which comprise:
  (a) causing a predetermined volume of fresh dialysate to flow in a first closed circuit to said membrane and causing an equal volume of waste dialysate to flow from said membrane in said first closed circuit,
  (b) causing a predetermined volume of fresh dialysate in a separate, second closed circuit to flow to said membrane, and causing an equal volume of waste dialysate to flow from said membrane in said second closed circuit,
  (c) sequentially operating said first closed circuit and said separate second closed circuit in alternation with each other, and (d) removing a further volume of said waste components after they have flowed through said semipermeable membrane.

50. The method defined in claim 49, including the further step of taking off the fluid flowing through the membrane.

51. The method defined in claim 50, including the further step of measuring the amount of the fluid taken off.

* * * * *